United States Patent [19]  
Chateau

[11] 4,071,315  
[45] Jan. 31, 1978

[54] ANALYTICAL TAPE MEDIUM

[76] Inventor: Guy Chateau, 7, rue des Ponts de Comines, Lille (Nord), France

[21] Appl. No.: 704,694

[22] Filed: July 12, 1976

[30] Foreign Application Priority Data

June 2, 1976 France .................................. 76 17634

[51] Int. Cl.$^2$ ...................... G01N 33/16; G01N 21/30
[52] U.S. Cl. .............................. 23/230 B; 23/253 R; 253/TP; 195/103.5 A
[58] Field of Search ............... 23/253 R, 253 TP, 259, 23/230 R, 230 B; 195/103.5 A

[56] References Cited

U.S. PATENT DOCUMENTS

| 3,261,668 | 7/1966 | Natelson | 23/253 R |
| 3,497,320 | 2/1970 | Blackburn | 23/253 R |
| 3,508,879 | 4/1970 | Findl et al. | 23/253 R |
| 3,607,079 | 9/1971 | Maxon et al. | 23/253 X |
| 3,620,678 | 11/1971 | Guigan et al. | 23/253 R |
| 3,676,080 | 7/1972 | Richterich | 23/253 R |
| 3,918,910 | 11/1975 | Soya et al. | 23/253 R |
| 3,932,133 | 1/1976 | Ishikawa | 23/253 R |

Primary Examiner—R.E. Serwin  
Attorney, Agent, or Firm—Robert E. Burns; Emmanual J. Lobato; Bruce L. Adams

[57] ABSTRACT

A method and apparatus is provided for the continuous immunological analysis of a plurality of samples of serum, which consists in detecting, in each sample, the possible presence of antibodies or antigens by fixation of the said antibodies or antigens possibly contained in the serum on a substrate of the corresponding antigens or antibodies thereto respectively, wherein the substrate is fixed on at least one zone of a longitudinal tape and by the fact that a longitudinal translatory displacement of the tape is effected in order to bring said zone, in succession, opposite a station where there is deposited a sample possibly containing the antibodies or antigens from said sample, in order to cause the fixation of these on the substrate fixed on the tape;

opposite a station in which the said zone is rinsed to eliminate any excess of unfixed antibodies or antigens or extraneous material;

and then opposite a reaction reading station.

20 Claims, 2 Drawing Figures

ANALYTICAL TAPE MEDIUM

The invention relates to a tape intended for use as a medium for a reaction, such as chemical or biochemical, for purposes of analysis and to an analysing process using the said tape.

The tape has the special feature that it has a reaction area capable of fixing one or more reagents and allowing the reaction to develop, and data storage facilities, allowing a series of specimens to be deposited and treated in the reaction area and the recording of data relating to the specimen and the reaction procedure, Automation application of complex treatment processes by chemical or biochemical reactions without risk of error in identifying the specimens and the reactions in progress.

The present invention relates to a tape intended for use as a medium for reaction, chemical or biochemical for example, for analysis purposes, and also to an analysis process using the said tape.

These past few years have seen the development of radioisotopic and enzymatic techniques for locating antigens or antibodies in the sphere of immunology, for hormone and biochemical dosages, etc....

The principle behind these particularly sensitive techniques is to combine an isotope such as I 125 1 or an enzyme such as peroxydase with molecules capable of reacting with the substance which it is wished to reveal. In the former case, the intensity of the radio-activity is measured after rinsing and eliminating the radio-active molecules which have remained free; in the latter case, the presence of enzyme is materialised by the addition of a specific substratum which takes on colour when in contact with the enzyme. The intensity of the residual radio-activity or of the colouring is proportional to the amount of substance tested for.

These techniques allow of a considerable increase in the sensitivity of reactions by making them easier to read, but they do call for many more manipulations of the sample being treated.

Indeed, when testing for anti-bodies in a serum, the following is an example of the procedure adopted. After pouring a solution of antigen corresponding to the anti-body sought into a tube made of a material allowing of passive fixation of the antigens, such as polystyrene, the said tube is then rinsed and the antigen remains fixed on its walls; into the tube is then placed the serum to be analysed and any anti-bodies which it may contain are fixed on the antigen which itself is fixed on the tube walls; the tube is once more rinsed to eliminate excess anti-body not fixed before proceeding to read the result of the reaction. As a general rule, any positive reaction cannot be read directly, and its positive character has to be amplified prior to the reading; to render any positive reaction visible, there is introduced into the tube a solution of an anti-globulin suitable for fixing on the anti-body sought, coupled with a radio-active or enzymatic element which thus enters into combination, via the anti-globulin, with the anti-body - itself fixed on the tube wall via the antigen; after further rinsing to eliminate the anti-globulin and the unfixed active elements, a direct reading is taken if the active element is radio-active or, if it is an enzyme, this latter is coloured with a suitable substratum and the reaction is read by colorimeter.

By associating in this way and active element with the anti-bodies looked for, the sensitivity of the reaction is multiplied some 10,000 times.

Unfortunately, the numerous manipulations required, notably by the successive rinsings, entail a risk of error in identifying specimens and reactions in progress when it is considered that a large number of samples are usually treated at the same time and that specimens from the same serum may simultaneously undergo several different analysis treatments.

In the specific case quoted above, such manipulations would also appear not to lend themselves readily to automation, and the rate of analyses carried out in this way rarely exceeds 60 an hour.

In the case of other analytical processes, use may be made of automatic machines such as those marketed under the trade names ABBOT or KONTRON, but these automatic machines do not eliminate the risks of a wrong identification of the specimen since this latter, placed either in a cup passing through the machine on in a micro-agglutinating tray, follows and precedes other specimens and can only be identified as to its origin and the treatment which it has undergone or is to undergo by means of coordinates which may give rise to errors.

An initial object of the invention is therefore to propose a new process and new means of analysis, or more generally of, for example, chemical or biochemical reactions, avoiding any error in identifying the specimens being treated and the treatments they are being or have been given.

Another aim of the invention is to allow of the automation of complex treatments by chemical or biochemical reactions such as that quoted as an example despite the numerous operations inovolved.

These two aims are achieved in accordance with the invention by depositing each specimen to be analysed and by applying each reaction which it must undergo on a tape which has a reaction area for this purpose, the said tape also having data storage facilities whereby there can be recorded opposite the tape reaction area relating to the specimen any details of the said specimen and of the treatment it is undergoing; these details accompany the specimen throughout its treatment without any possible identification error and can even, if necessary, control the treatment process.

The process as per the invention allows of full automation of all the reaction stages, notably in the example quoted above where the absence of handling and the certainty of identifying specimens allows the hourly rate to be increased to 300 analyses. Speaking quite generally, the process as per the invention allows of full automation, with certainty of identification of the specimens treated and the treatments undergone, of all types of tests including those which use isotopes or enzymes or any other substance having an amplifying effect on the positive or negative character of the result obtained.

The tape as per the invention, intended for use as a medium for a chemical or biochemical reaction, for instance, as a means of analysis, has the special feature that it comprises at least a reaction area allowing of the fixation of at least one of the reaction substrata and data storage facilities, making it possible respectively to deposit and process several specimens placed side by side along the tape and to record simultaneously items of information regarding each specimen and/or the treatment which it is to be given.

The invention will be better understood if reference is made to the description below and to the attached drawings relating to a non-limitative method of producing the tape and to a non-limitative method of applying a processs of analysis using the said tape.

Figure 1:
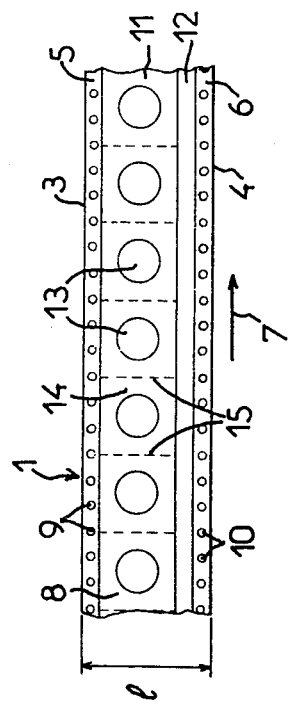
FIG. 1 shows a view from above of a length of tape as per the invention.

FIG. 1 shows at (1) the tape as per the invention which takes the form of a strip with a constant width $w$ and a length which is usually considerable in relation to the said width $w$; this tape may, for instance, be stored in the wound state in a cartridge 2 (shown in schematic form in FIG. 2) from which it can be unwound at will and in accordance with requirements; this cartridge 2 may be at least partially transparent or, if opaque, provided with a window for checking the amount of tape wound on the inside.

Here along each of its lengthwise edges 3 and 4, the tape 1 comprises a strip, respectively 5 and 6 intended to engage with drive arrangements causing it to travel forward along its general direction 7. These drive arrangements may consist of rotating wheels bearing on at least one of the faces 8 of the tapes at these lateral strips 5 and 6 in a self evident manner; likewise in a self evident manner, in order that the position of each area of the tape be absolutely determined at a given moment, these wheels are cogged and consequently the two lateral strips 5 and 6 of the tape 1 are provided with perforations, respectively 9 and 10, repeated at intervals over the length of the tape 1 in its lateral strips 5 and 6.

Between the strips 5 and 6, the tape is again subdivided over its width into two lengthwise strips 11 and 12, the first of which, usually wider, is intended to take the substrata to be treated, the treatment substrata, and constitute the base for the same, and the second is intended for storing data relating to the substratum being treated, the treatment which it is to undergo or has undergone, etc...

The data storage strip 12 may very well consist of a magnetic or optical recording and reading track of any known type or again of a track which can be perforated with a view to optical or mechanical reading, etc..... This track may be added to the tape subsequently or form an integral part thereof.

The reaction strip 11 may be of any material allowing of the active or passive fixation by any linking process which is not of a denaturing character of at least one of the bodies required for the reaction used in the analysis for which the tape is intended.

Moreover one of these bodies may be fixed on the reaction strip 11 prior to placing the tape 1 in the cartridge 2, the latter being so designed as to ensure the proper preservation of the tape and the bodies which it carries, protecting them from contamination, damp, etc.

In this way there may be fixed to strip 11 of tape 1 antigens or anti-bodies or any other body necessary for the given reaction to serve as a target for the substances looked for.

Preferably this body is fixed in the areas 13 of strip 11 evenly distributed over the length of the strip and separated from each other by a sufficient distance to prevent, when subsequently depositing the different substrata entering into reaction, any migration of one of these substrata from the area 13 for which it is intended to neighbouring areas, thus falsifying results.

Being porous or wettable in areas 13, the tape 1 is to this end preferably rendered water-repellent in areas 14 of the strip 11 separating the areas 13. This non-wettable property may be achieved for instance by appropriate treatment of the tape in its strip 11.

At least in its strip 11 and more precisely in the areas 13 of this latter, the tape 1 is preferably porous, notably so that it may lend itself to rinsing action by filtration through its texture, but it may equally well be non-porous in which case the rinsing actions can be effected by lateral flow of liquid over the tape surface; a porous surface however offers the advantage of increasing the contact surface offered to the different substrata used in the reaction. The tape may be opaque or transparent. Without importance as regards isotopic methods, the transparent nature of the tape on termination of reaction in the case of enzymatic methods allows of colorimeter reading by measuring the absorption of light through the tape in its reaction areas 13; it is however possible if necessary for this colorimeter reading to be effected by refractivity if the tape is not transparent.

The tape 1 should be generally flexible, notably to allow of its winding. To this end it may be of a flexible material, but it may take different forms where the flexible portions alternate with rigid portions which correspond, for instance, to the areas 13; amongst other things, it may take the form of a continuous film or a succession of small flexibly joined plaquettes.

In practice, good results have been obtained by using a tape 1 made of synthetic plastic material such as polystyrene or polypropylene in film form rendered porous or otherwise or in the form of woven threads or of a cellulose base material such as paper, the said materials coming in transparent form or otherwise.

It appeared advantageous to provide along the tape pre-cut transversal lines 15 located between the reaction areas 13 in order to make it more easy to detach with the minimum of waste the length of tape used from that which, not being used, should preferably remain inside the cartridge 2.

The use of such a tape in searching for a given antibody in samples of serum will now be described with reference to FIG. 2.

Preferably, the tape used for this purpose and which is for example of the type illustrated in FIG. 1 carries, fixed in its areas 13 the antigen likely to fix the anti-body looked for.

This tape 1 is unwound and taken out of its cartridge 2 as required by means of toother wheels such as 16 engaged in the perforations 9 and 10 of the lateral strips 5 and 6. Similar toother wheels suitably arranged then provide a drive from one treatment position to another at a constant travel speed over the tape length; during this forward travel movement, it is if necessary guided by slides not illustrated. On leaving the cartridge 2, the tape 1 thus passes below a station 17 for identifying, positioning and depositing the specimen to be treated.

This station provided for the simultaneous positioning of an area 13 below the sample-depositing needle 18 and the deposit of a sample, in this case a serum, onto this area 13.

In practice, the accurate positioning of the area 13 below the needle 18 is detected by reading a mark, which may be optical for instance, carried by the tape and using a reader which may, for example, be integral with the station 17.

Once the area 13 is positioned exactly below the needle 18, the specimen, in this case serum, is deposited from a sample dispenser 24 by means of a pump which may, for example, be reciprocating or peristaltic, with rinsing of the needle between two successive specimens in order to avoid contamination.

The means for applying these stages of the process are self evident and will not be enlarged upon.

If the tape is porous, at least in its areas 13, penetration of the specimen of serum into the tape can be improved by vacuum suction through the tape using a device shown in schematic form at 19 and fitted opposite the needle 18.

It should be noted that specimen-depositing stations such as 17 may be multiplied in order to improve the performance of the machine or to carry out several simultaneous analyses on the same specimen. In the former case, the successive areas 13 carry the same antigen; in the latter case, the areas 13 which follow each other carry different antigens corresponding to the different reactions to be carried out on the same specimen, but with the identical areas 13 recurring periodically along the tape to allow of the successive treatment of several different specimens using the same tape. In both cases, once the successive specimen-depositing devices have fulfilled their function, the tape 1 must progress by a number of areas 13 equal to the number of simultaneous deposits before there can be a fresh deposit of samples. Simultaneously with the deposit of a specimen in an area 13 of the tape, a device also integral with station 17 and associated with a reading device at the sample dispenser 24 records on the data storage strip 12 the number of the sample deposited opposite the area 13 which has received it.

It should be noted that the different functions provided for at atation 17, namely the positioning of the area 13 below the needle 18, the depositing of the sample on the said area 13, the reading and recording of the sample number and any suction through the area 13 can be applied by one or more successive modules.

Accessorily, provision may be made between the station 17 and the operating cartridge 2 for a tape cutting device allowing only the number of areas 13 required by the number of samples to be treated to be used.

On leaving station 17, the sample, here of serum, deposited on an area 13 comes into contact with the antigens orginally fixed on that area.

The fixation of the specifically active parts of the serum, that is to say any anti-bodies which may be contained therein, requires in order to achieve an optimum level of efficiency a more or less lengthy period which is ensured by routing the tape 1 zigzag fashion through an incubation enclosure 20 thorugh which the tape passes immediately after station 17.

This zigzag trajectory is provided by a guide system comprising slides (not shown) and drive rollers 21 in this case toothed. The number of these rollers is variable to allow for variable incubation times appropriate to each type of test. If required, the enclosure 2 can take several tapes 1 laid side by side in the crosswise direction.

Inside the enclosure 20, the atmosphere is controlled, notably for humidity and temperature, by any method.

If necessary, there may enter into this enclosure the needle 22 of a device 23 allowing the deposit of any reagent desired onto an area 13 once this is immediately below the needle 22. This device 23 may be identical or similar to the specimen-depositing device; where necessary, the nature of the reagent deposited by this device 23 can be recorded on the strip 12 simultaneously with the depositing action. This device 23 may also be controlled by data previously recorded on the strip 12, for instance at station 17 when the specimen is deposited or during the manufacture of the tape 1 prior to its storage in the cartridge 2.

When the area 13 leaves the incubation chamber 2, any anti-bodies which may be contained in the specimen of serum are fixed onto the antigens originally fixed in the tape areas 13.

Strip 11 of the tape then passes through a rinsing station 25 one of whose purposes is to eliminate excess free anti-bodies. If the areas 13 of the tape are porous, this rinsing can be done through these areas; in such event, the rinsing station 25 which, for the purpose of depositing the rinsing fluid has a needle 26 mounted above the obligatory passage of the strip 11 of the tape, is completed by a suction device 27 fitted opposite the needle 26 but on the other side of the tape to simplify the operation. If on the other hand the tape is impermeable in these areas 13, the rinsing is done by lateral flow of liquid over the tape surface with "trapping" of the rinsing liquids.

After the rinsing station 25, the tape next passes through a station 28 for depositing the radio-active or enzymatic compound intended to play the role of amplifier of the reaction result.

This station 28 has an identical device to that depositing the specimen at 17, with a needle 29 leading to above the strip 11 of the tape to deposit the radio-active or enzymatic compound in its areas 13, and if necessary a vacuum suction device 30 arranged below the tape opposite needle 29 to encourage the penetration of the compound into the thickness of area 13 if that is porous.

The operating of the rinsing and compound depositing stations 28 is preferably controlled, once an area 13 is accurately positioned below the depositing needle 26 or 29 of the station, by data recorded on the strip 12 of the tape either while this is being made or at the sample depositing station 17.

Furthermore, there can be recorded on this strip 12 at station 28 details of the compound deposited in such a way as to control the operation of the stations which the tape subsequently passes through.

Figure 2:
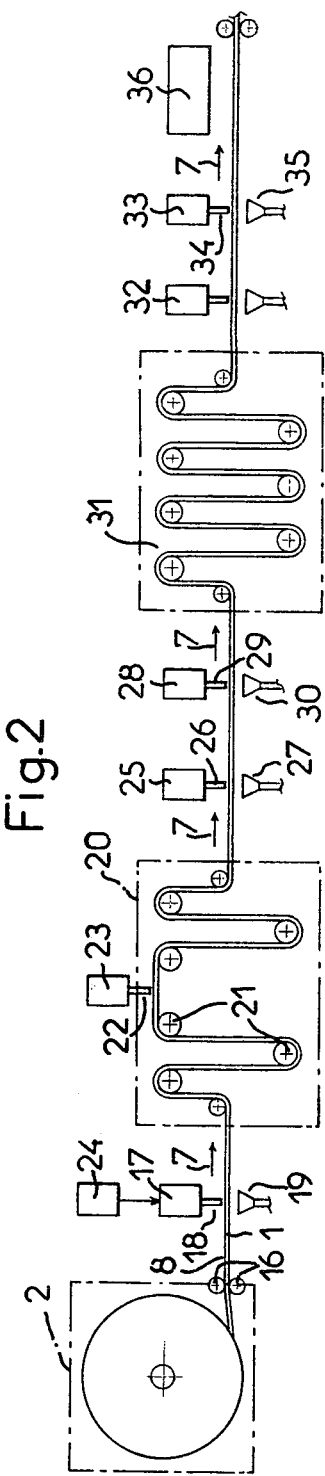
FIG. 2 illustrates schematically a process for detecting antibodies in a serum using such a tape.

In effect, the result of the reaction can be read directly, after fixing and rinsing, when a radio-active compound is used whereas the use of an enzymatic compound necessitates, after a certain incubation time necessary for fixation to the anti-bodies followed by a rinsing, the deposit of a colouring substratum before the reading can be taken: the device described and illustrated in FIG. 2 comprises the successive stations corresponding to these different phases of the treatment of the strip when use is made of an enzymatic compound to reveal the result of the reaction, but the station which deposits the coloured substratum should only operate when an enzymatic compound has been deposited at 28.

Consequently, the arrangement illustrated in FIG. 2 comprises, downstream of station 28 in relation to the direction of travel 7 of the tape, an incubation enclosure comparable to the incubation chamber 20 and in which there takes place, in an atmosphere which is controlled more especially as regards humidity and temperature, the fixation of the radio-active or enzymatic compound onto any anti-bodies which may have fixed on the antigen in areas 13 of the tape.

This incubation enclosure 31 is followed by a rinsing station 32 identical to rinsing station 25 and which provides for the elimination of any of the compounds remaining free following the incubation period provided by the passage through the enclosure 31.

This rinsing station 32 is followed by a colouring substrata depositing station 33, this station only operating when a composite reading device detects both the accurate positioning of an area 13 below the depositing needle 34 of the said station and the information previously recorded on the strip 12 to indicate the depositing of an enzymatic compound.

Like the rinsing station 32, in the same way as the different successive depositing or rinsing stations 17, 25, 28, station 33 has a vacuum suction device opposite depositing needle 34 and on the other side of the tape to facilitate the deep penetration of the substratum when a tape is used with porous areas 13.

Since the development of colouring may require a certain incubation time, in the region of 1 hour in the example chosen, provision may be made for an enclosure similar to the enclosure 31 after station 33 (this station has not been shown).

When an enzymatic process is adopted and use is made of a tape which is opaque, notably in areas 13, there may be added to the equipment a station for rendering the said areas 13 transparent by depositing an appropriate substance, depending on the nature of areas 13, prior to the passage of area 13 in front of the reaction result reading station 36.

The substance conferring the transparency can be deposited by passing in front of a station identical to station 33 and positioned before or after this latter in relation to the direction of travel 7.

The colorimetric or isotopic reading station 36 comprises two sub-modules,

The first sub-module reads the strip 12 of the tape in order to identify the specimen, for instance by its number recorded at station 17, and where necessary to identify the nature of the different substrata deposited during the process, with a view to transmitting these details to a printer, a storage memory or any kind of computer system.

A second module measures the intensity of the reaction, for instance by means of a crystal well in the case of an isotopic process or a colorimeter in the case of coloured enzymatic reactions. This measuring module is linked to a recorder or computer or printer or a combination of all three which connect up the result of the reaction to the characteristics of the specimen and of its treatment as identified by the first module.

It should be noted that this facility for computer processing of results can considerably speed up the tracking down operations on a great many specimens.

The arrangement described corresponds of course to a particularly simple instance of using the process as per the invention, but this process is open to more complicated developments with the use of a tape similar to that described in FIG. 1 providing the same facilities and the same speed of treatment without human intervention between the depositing of the specimen to be tested and the output of the result, and the sure identification of each specimen and of the treatment it has undergone.

An example is given below of the application of the process when testing for the antigen Australia.

The tape used 1 has areas 13 consisting of several layers of polystyrene fabric on which there have been fixed anti-Australia globulins known as "anti-hepatitis B surface" or "anti HBS".

The specimen is taken and deposited at station 17 on an area 13. The amount deposited is in the region of 100 microliters.

The tape passes through the enclosure 20 at 37° C for about 1 hour; the mixing process achieved by the vertical zigzag travel encourages contact between the HBS antigens and the anti-bodies fixed on the backing 13.

On leaving the enclosure 20 there is copious rinsing with a 9°/°° solution of NaCl (station 25).

At station 28 there is added a compound IgG (immunoglobulin type G) consisting of alkaline anti HBS-phosphatase (approximately 100 microliters are required). The compound is prepared by combining 0.5 mg of IgG antiHBS and 1.5 mg of alkaline phosphatase treated with glutaraldehyde or benzoquinone purified by chromatography.

The compound fixes onto the antigen thanks to the anti-body part. This fixation is developed at 37° for approximately 1 hour in the enclosure 31.

Fresh rinsing takes place at station 32 with saline solution.

At 33 there is deposited a solution of para-nitrophenylphosphate (approximately 100 microliters at a 1mg/ml concentration).

On contact with the alkaline phosphatase fixed at 13, the p.nitrophenylphosphate is transformed into yellow para-nitrophenolate. The development of this colouring takes place in an enclosure similar to enclosure 31 (not shown here) for approximately 1 hour at 37° C. At the exit from this enclosure, at 36, there is a colorimeter which measures the linear absorption through the tape, at 13, at a wavelength of 420 nm. Simultaneously, a reading is taken of the specimen number and the analysis number stored at 12.

The result is printed out on a stylo linear recorder or on a printer giving all the information stored, or on a small additional computer which inteprets the result in the light of the positivity thresholds previously calculated with check specimens.

The whole of the reactions take approximately 3 hours. The time may probably be shortened because of the greater degree of contact achieved by using a tape for the development of the reactions instead of a smooth-surfaced polystyrene tube.

In the case of an isotopic reading, the compound is replaced by an anti-body marked at I 125 and the reaction can be interpreted after only 2 hours.

This is a non-limitative example. The process as per the invention may be used when looking for anti-bodies developed during all infectious diseases of bacterial, fungic, viral or parasitic origin, in hormonology the anti-bodies occurring in any biological fluid: blood, urine, etc.

I claim:

1. A method for the continuous immunological analysis of a plurality of samples of serum, which consists in detecting, in each sample, the possible presence of a first substrate of antibodies or antigens by fixation of the said first substrate possibly contained in the serum on a second substrate of the corresponding antigens or antibodies respectively, wherein the second substrate is fixed on at least one zone of a longitudinal tape and by the fact that a longitudinal translatory displacement of the tape is effected in order to bring said zone, in succession, opposite a station where there is deposited a sample possibly containing the first substrate, in order to cause the fixation of the possible first substrate on the second substrate fixed on the tape, opposite a station in which the said zone is rinsed to eliminate any possible excess of unfixed first substrate, and then opposite a reaction reading station.

2. The method according to claim 1, wherein the said fixation of the first substrate on the second substrate is brought about by causing the tape to pass, between the depositing station and the rinsing station, through an incubation enclosure, the temperature and hygrometric degree of which are controlled.

3. The method according to claim 1, wherein between the rinsing station and the reading station, said zone of the tape is conducted opposite a station where there is deposited a third substrate which amplifies the reaction and is capable of being fixed on the first substrate in order to cause the fixation of said third substrate on the first substrate possibly fixed on the second substrate which, in its turn, is fixed on the tape, and then opposite a second rinsing station where the unfixed excess third substrate is eliminated.

4. A method according to claim 3, wherein said fixation of the third substrate on the first substrate is brought about by causing the tape, between the station for the depositing of the third substrate and the second rinsing station, to pass through an incubation enclosure the temperature and the hydrometric degree of which are controlled.

5. A method according to claim 3, the first substrate being an antibody wherein the third substrate is an antiglobulin suitable to be fixed on said antibody which is being sought, coupled with a radioactive element to permit an isotopic reading of the reaction.

6. A method according to claim 3, the first substrate being an antibody, wherein third substrate is antiglobulin suitable to be fixed on the said antibody which is being sought, coupled with an enzyme, and by the fact that the said zone of the tape, prior to the reading, is brought opposite a station where there is deposited on it a colored substrate capable of being fixed on the said enzyme in order to permit a colorimetric reading.

7. A method according to claim 6, wherein the tape, between the station for the depositing of the colored substrate and the reading station, is caused to pass through an incubation enclosure the temperature and hygrometric degree of which are controlled.

8. A method according to claim 5, the tape being opaque in the said zone and the reading of the reaction being effected by transparency, wherein said zone of the tape is brought opposite a station where it is made transparent prior to the reading.

9. A method according to claim 7 wherein the tape is passed zig-zag through the incubation enclosure.

10. A method according to claim 1, the tape being porous, wherein the rinsing is effected by causing the tape to pass, in said zone, through a rinsing fluid.

11. A method according to claim 10, wherein said rinsing fluid is aspirated through said zone.

12. A method according to claim 1, the tape being impermeable in said zone, wherein the rinsing is effected by lateral flow of a rinsing fluid on the surface of the tape.

13. The method according to claim 1, the tape being provided with information storage means, wherein an information characteristic of the sample treated is introduced into the information storage means simultaneously with the depositing of the sample on the reaction zone in order to permit a subsequent combined reading of the said information and of the result of the reaction.

14. The method according to claim 1, the tape comprising storage means for information, wherein information directing the travel of the tape and the operation of the different stations is introduced into the information storage means.

15. The method according to claim 1, the tape being porous at least in its reaction zone, wherein the step of the depositing of a substrate on it is accompanied by aspiration through it.

16. The method according to claim 1, wherein said tape comprises at least one reaction zone, wherein at least the said zone comprises a material suitable to permit the fixation of the second substrate of antigens or antibodies respectively therein.

17. The method according to claim 16, wherein the material which at least constitutes said zone portion of said tape is selected from among polystyrene, propylene, and paper.

18. The method according to claim 16, said tape being porous, at least in the said zone.

19. The method tape according to claim 18, wherein said tape is comprised of woven thread, at least in the said zone.

20. The method according to claim 16, wherein said tape is provided with portions adapted as information storage means.

* * * * *